United States Patent [19]

Forrester et al.

[11] Patent Number: 4,590,206

[45] Date of Patent: May 20, 1986

[54] INHALATION PHARMACEUTICALS

[75] Inventors: Raymond B. Forrester, Sandbach; Terence D. Boardman, Northwich, both of England

[73] Assignee: Fisons plc, Ipswich, England

[21] Appl. No.: 606,542

[22] Filed: May 3, 1984

Related U.S. Application Data

[63] Continuation of Ser. No. 399,748, Jul. 19, 1982, abandoned.

[30] Foreign Application Priority Data

Jul. 24, 1981 [GB] United Kingdom ............... 8122846

[51] Int. Cl.$^4$ ............................................. A61K 31/35
[52] U.S. Cl. .................................... 514/456; 514/826; 514/951
[58] Field of Search ................ 424/283; 514/456, 826, 514/951

[56] References Cited

U.S. PATENT DOCUMENTS 3,957,965  5/1976  Hartley et al. ..................... 424/14
4,161,516  7/1979  Bell ..................................... 424/14

OTHER PUBLICATIONS

Lachman et al., "The Theory and Practice of Industrial Pharmacy", 2nd ed., 1978, pp. 519-524.

*Primary Examiner*—Leonard Schenkman
*Attorney, Agent, or Firm*—Marshall, O'Toole, Gerstein, Murray & Bicknell

[57] ABSTRACT

There is described a finely divided inhalation drug, e.g. sodium cromoglycate, comprising a therapeutically effective proportion of individual particles capable of penetrating deep into the lung, characterized in that a bulk of the particles which is both unagglomerated and unmixed with a coarse carrier, is sufficiently free flowing to be filled into capsules on an automatic filling machine and to empty from an opened capsule in an inhalation device. A number of the individual drug particles have a spherical, collapsed spherical or ring doughnut shape.

There is also described a method of making the fine particles and pharmaceutical formulations containing them.

10 Claims, 12 Drawing Figures

INHALATION PHARMACEUTICALS

This is a continuation of application Ser. No. 399,748, filed July 19, 1982, now abandoned.

This invention relates to a novel form of drug and to methods for its production and formulation.

In our British Pat. No. 1,122,284 we have described and claimed an insufflator device for use in the administration of powdered medicaments by inhalation. With that device, and other devices, e.g. that described in British Patent Specification No. 1,331,216, and European Patent Application No. 813021839 a user inhales air through the device which causes a powder container mounted therein to rotate. Powder within the container is fluidised and dispensed into the air stream which is inhaled by the user. For optimum dispensing it has been found that the powdered medicament particles should be comparatively free-flowing and yet should have an ultimate particle size of less than about ten microns to ensure adequate penetration of the medicament into the lungs of the user. These two requirements are prima facie mutually exclusive, since such fine powders are not usually sufficiently free-flowing. It has in the past been found that this problem can be mitigated or overcome, e.g. as described in U.S. Pat No. 4,161,516, by forming the powdered medicament into small soft pellets or soft granules. Both soft pellets and soft granules will fluidise satisfactorily within the container and yet are of sufficiently low internal coherence to break up into finer particles of medicament of a therapeutically effective size in the turbulent airstream around the outside of the container. However the procedure of forming the micronised drug into soft pellets or granules is both difficult and expensive. An alternative means of getting the fine particles to flow and disperse satisfactorily has been to mix them with a coarse carrier, e.g. coarse lactose (see U.S. Pat. No. 3,957,965). However with all pharmaceuticals it is desirable to use as pure a form as possible (inter alia to avoid any possible adverse reactions by the patient to the excipients) and the presence of the coarse carrier is not therefore desirable. Furthermore the mixing of the fine drug with the coarse carrier involves the extra expense of the carrier, the possibility of segregation of carrier and drug during transport and storage, and extra process steps which add to the cost of production. Production of both the pelletised material and the blend of fine material with the coarse carrier involves the initial step of micronising the drug. Sodium cromoglycate has been made, for blending with lactose or agglomeration into soft nearly spherical pellets and administration by inhalation, as a micronised dry powder and in this form consists mostly of rods or lath-shaped crystals. In both the pelletised and blended material energy is needed to break up the pellets or to separate the fine drug from the coarse carrier before or during inhalation. Thus in many instances it has also been found that the amount of drug which is available as fine particles in the air stream is dependent on the rate at which air is passed through the inhaler (i.e. the amount of energy imparted to the formulation). This can be particularly disadvantageous when the drug is used to treat patients suffering from conditions affecting their ability to breath.

Thus for many years the production of drugs in a form in which they can flow easily (and therefore be filled readily into capsules) while at the same time being of a sufficiently small particle size to penetrate deep into the lung has presented a problem which has only been capable of resolution by means of complex procedures.

We have now found particles which can penetrate deep into the lung and yet which are sufficiently free flowing to be filled into capsules, and otherwise manipulated, without mixing with a coarse diluent or formation into soft pellets or granules. We have also found that these particles can disperse well from an inhaler at both low and high air flow rates, thus, in certain circumstances, improving consistency of capsule emptying. Furthermore we have found that the new particles can, in general, be coarser than those of the prior art while giving an equivalent proportion of particles capable of penetrating deep into the lung.

According to the invention we provide a finely divided inhalation drug comprising a therapeutically effective proportion of individual particles capable of penetrating deep into the lung, characterised in that a bulk of the particles which is both unagglomerated and unmixed with a coarse carrier, is sufficiently free flowing to be capable of being filled into capsules on an automatic filling machine and to empty from an opened capsule in an inhalation device.

According to the invention we also provide a drug in finely divided and unagglomerated form, wherein a substantial proportion of the individual drug particles have a spherical, collapsed spherical, i.e. where one or both sides of the sphere appear to have been pushed inwards, or toroidal shape, i.e. the shape of a ring doughnut. The ring doughnut shapes may have a hole through the middle or may have a thin membrane filling the hole. In certain cases a population of two or more of spheres, partially collapsed spheres, fully collapsed spheres and ring doughnut shapes is found.

BRIEF DESCRIPTION OF THE DRAWINGS

The accompanying figures are electron micrographs of finely divided inhalation drugs produced in accordance with the invention, as follows.

Figure 1:
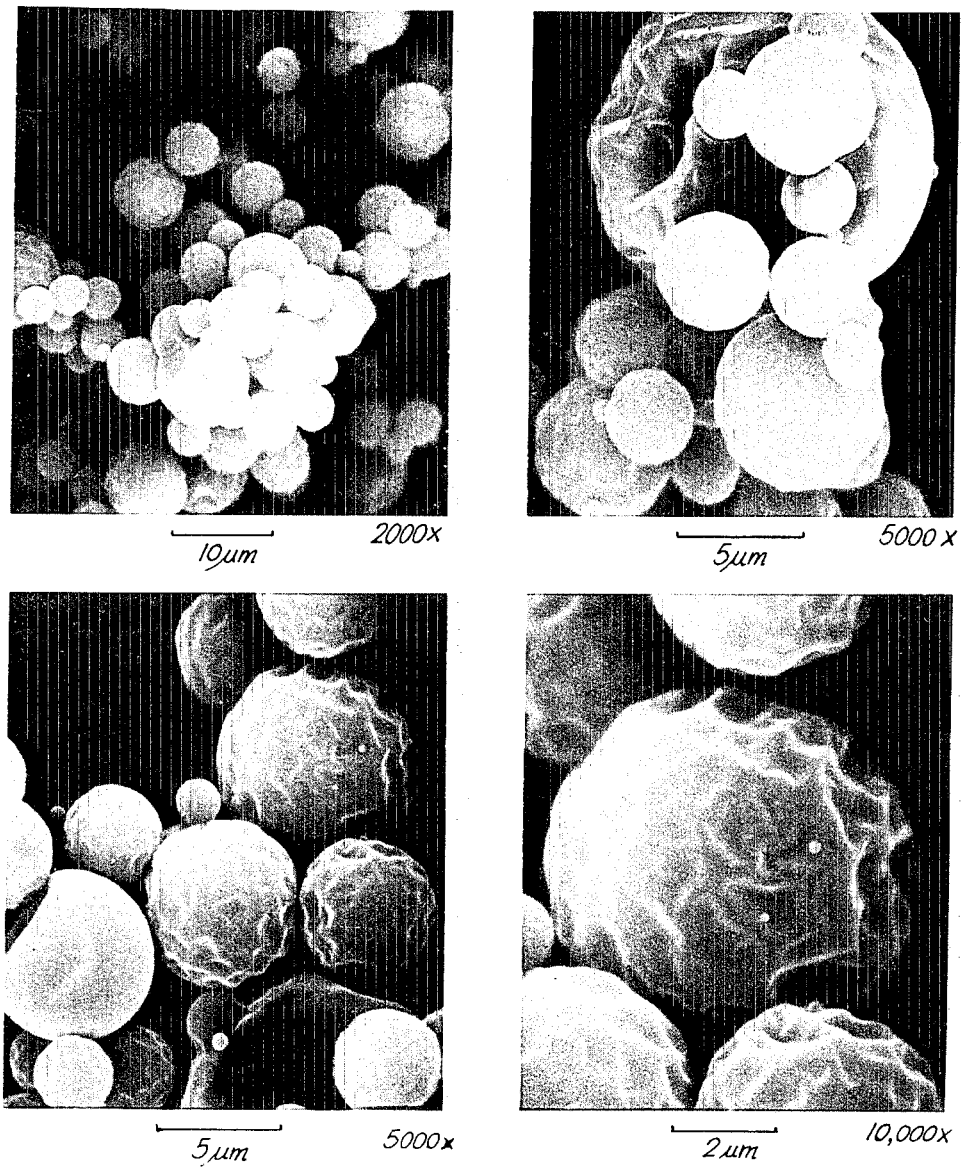
FIG. 1 shows terbutalene sulphate.
Figure 2:
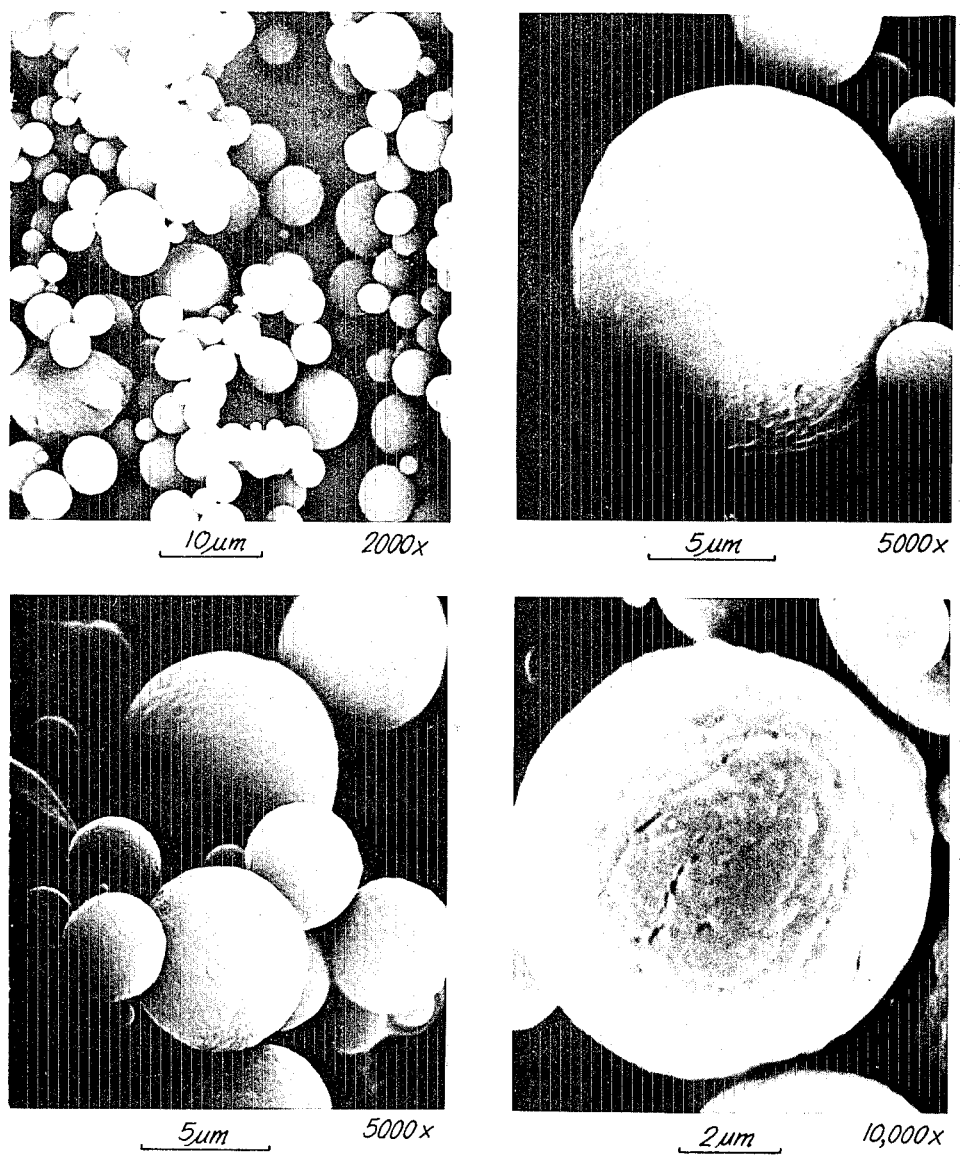
FIG. 2 shows 4,6-dioxo-10-propyl-4H,6H-pyrano-(3,2-g)pyran-2,8dicarboxylic acid disodium salt.
Figure 3:
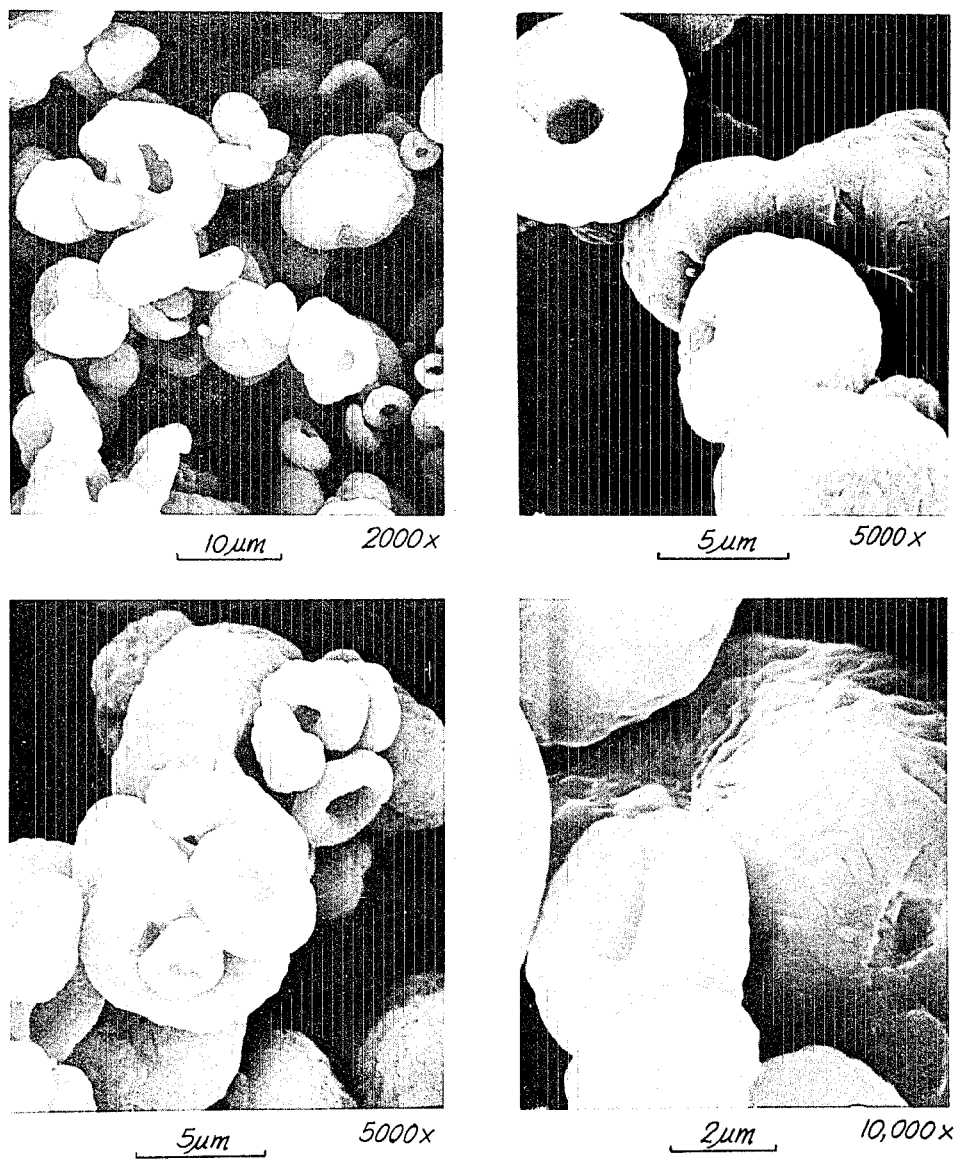
FIG. 3 shows terbutalene sulphate.
Figure 4:
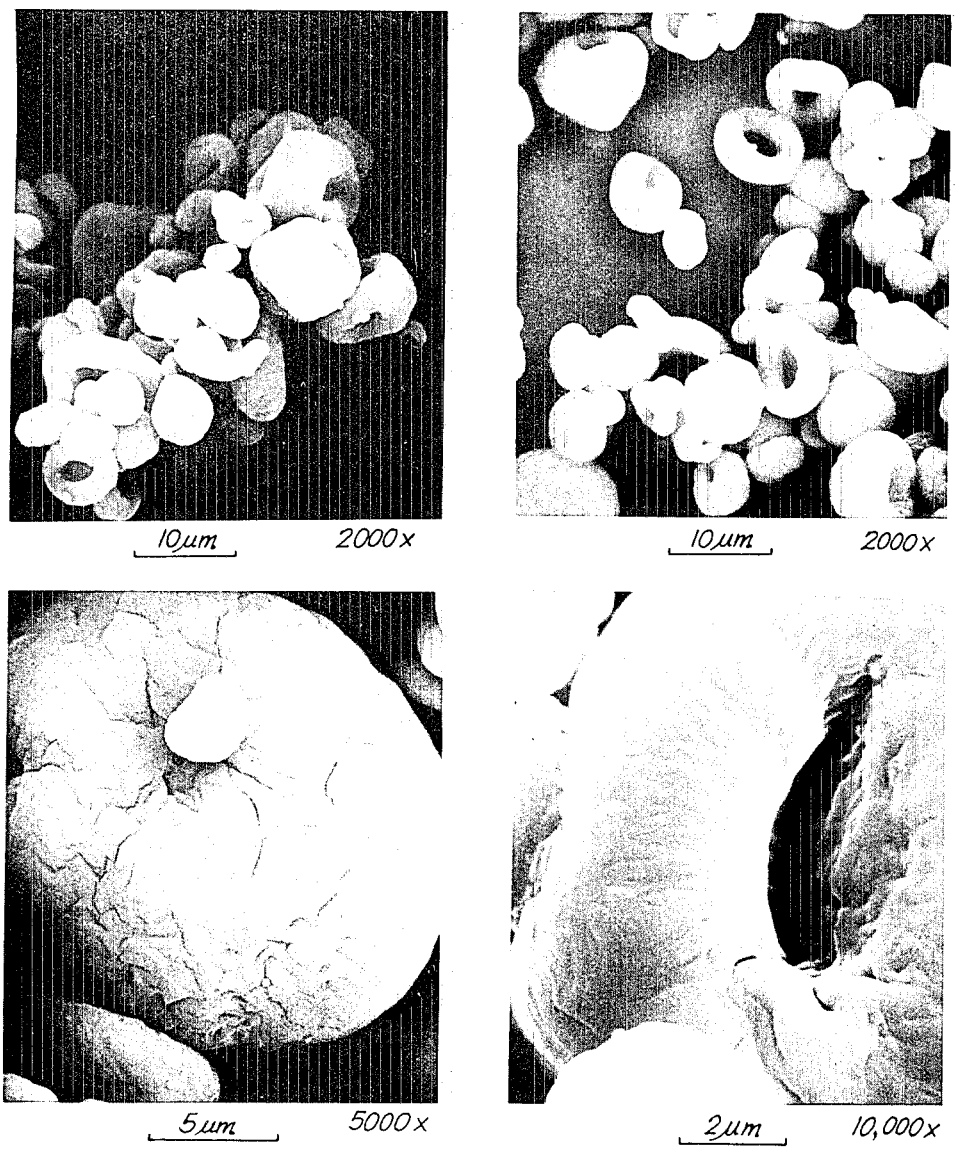
FIG. 4 shows isoprenaline sulphate.
Figure 5:
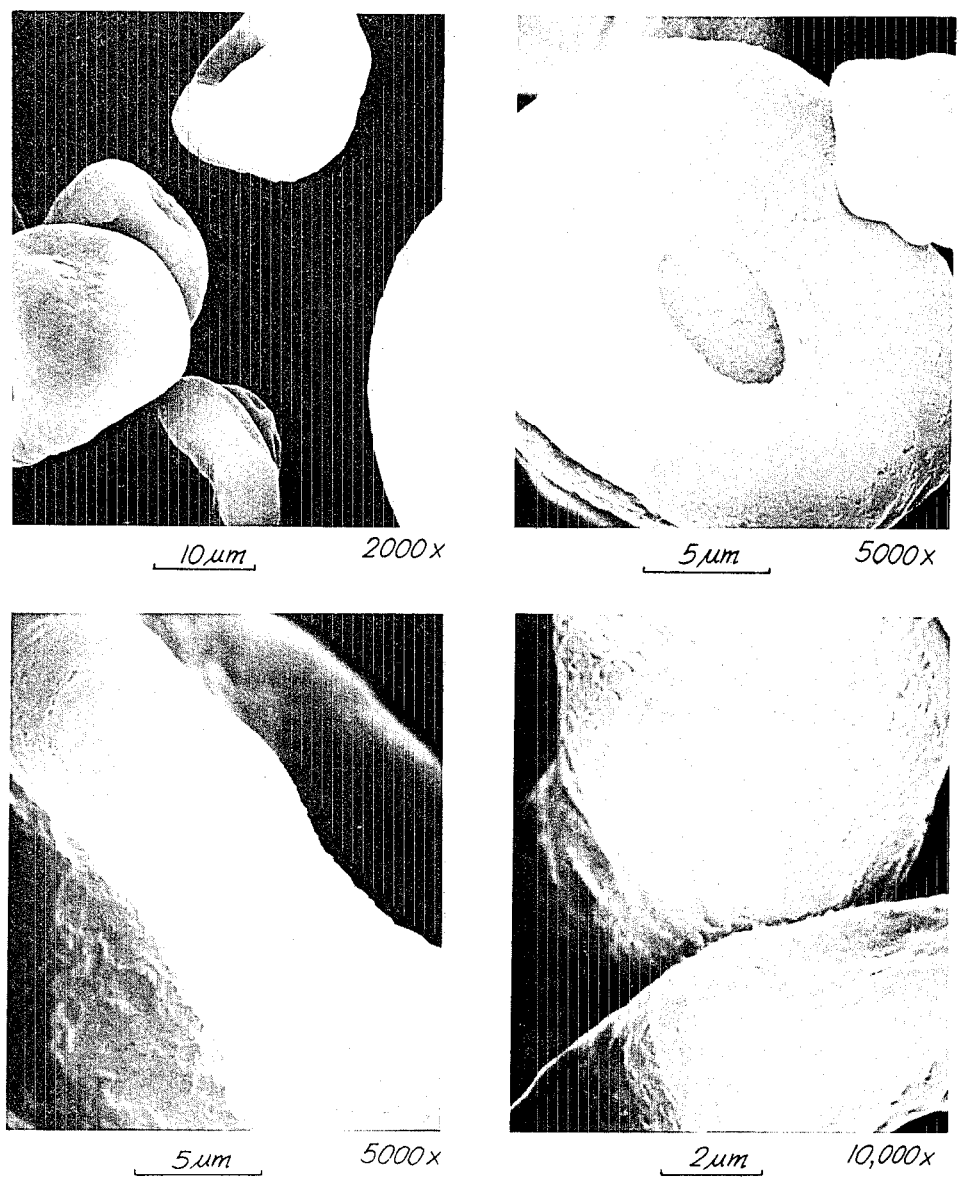
FIG. 5 shows sodium cromoglycate produced with a slotted disc atomiser.
Figure 6:
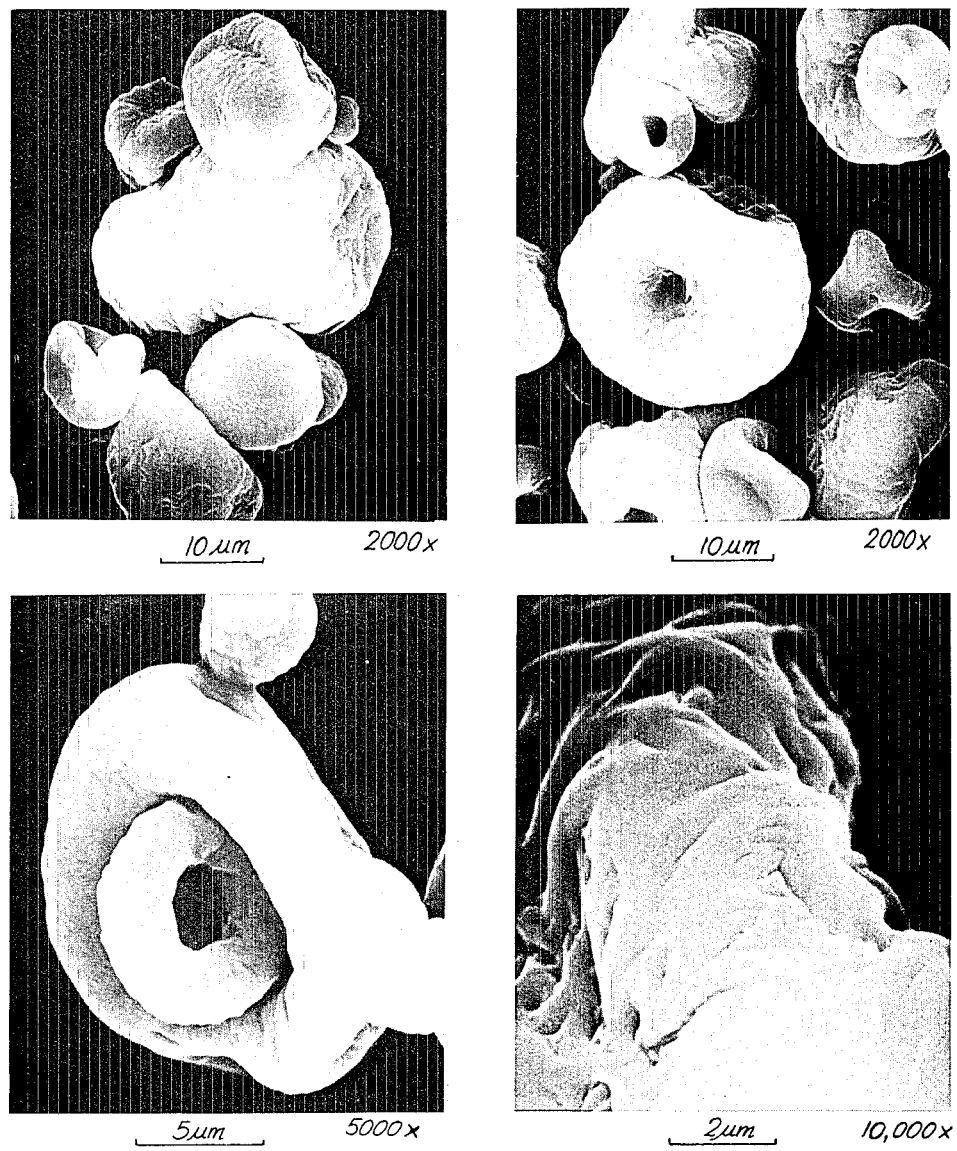
FIG. 6 shows sodium cromoglycate produced with an inverted cup atomiser.
Figure 7:
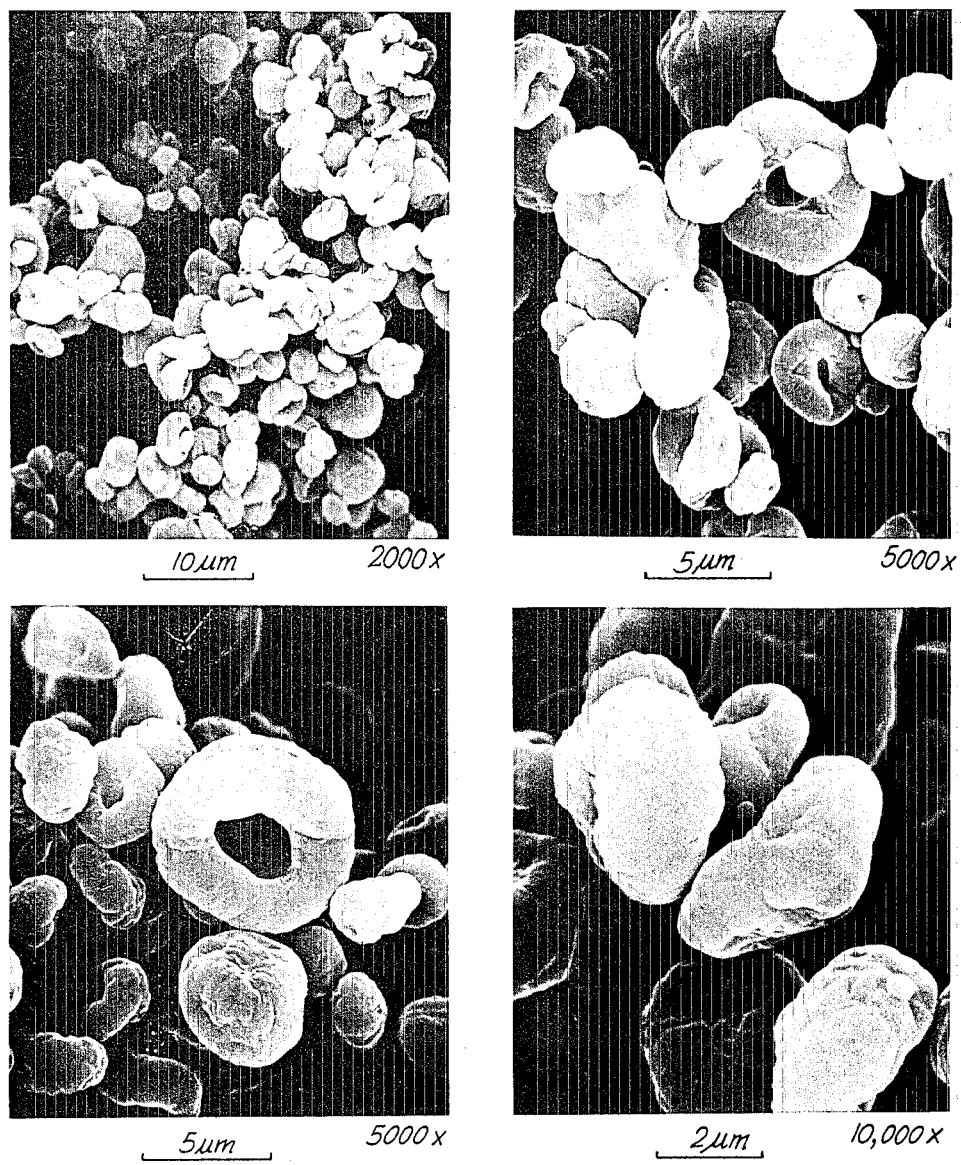
FIG. 7 shows sodium cromoglycate produced with a 4 mm orifice atomiser.
Figure 8:
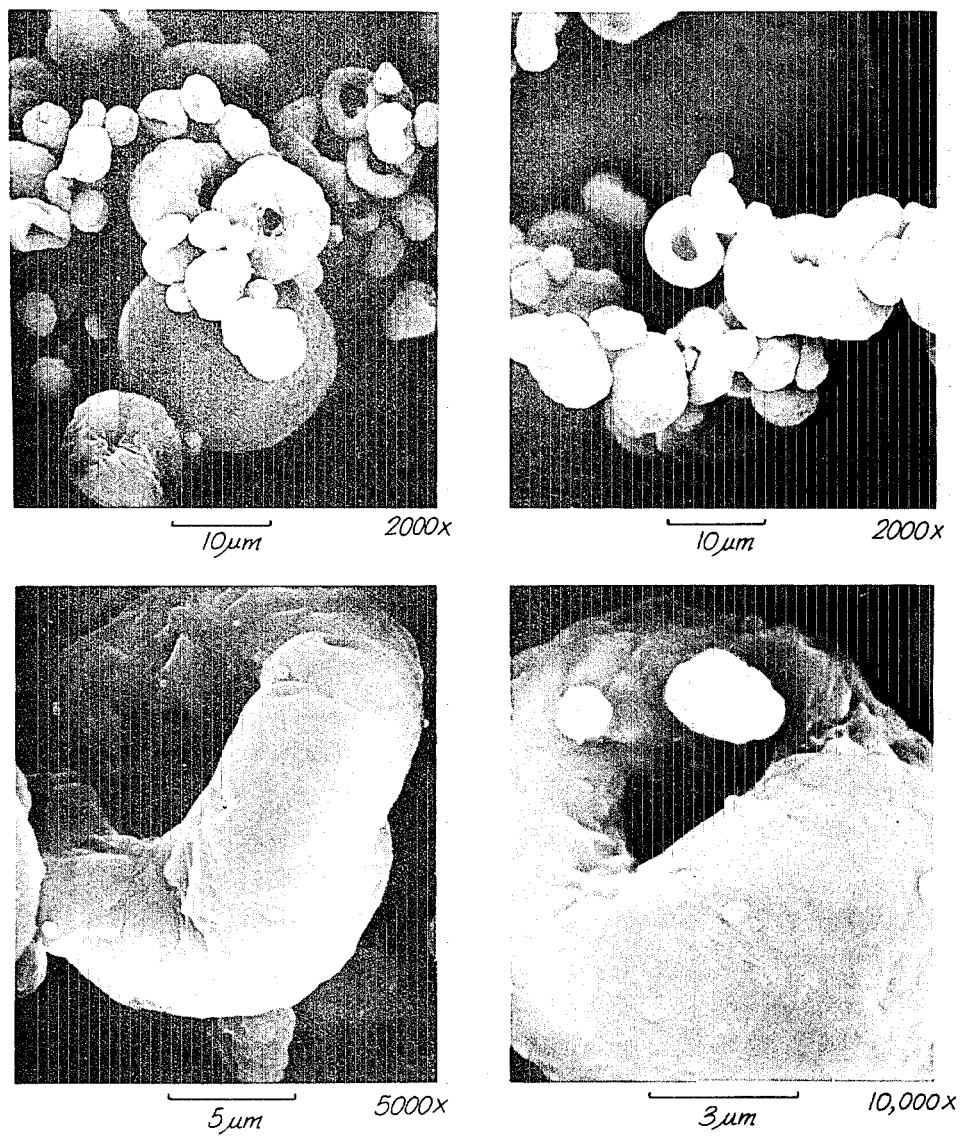
FIG. 8 shows sodium cromoglycate produced with an ultrasonic nozzle.
Figure 9:
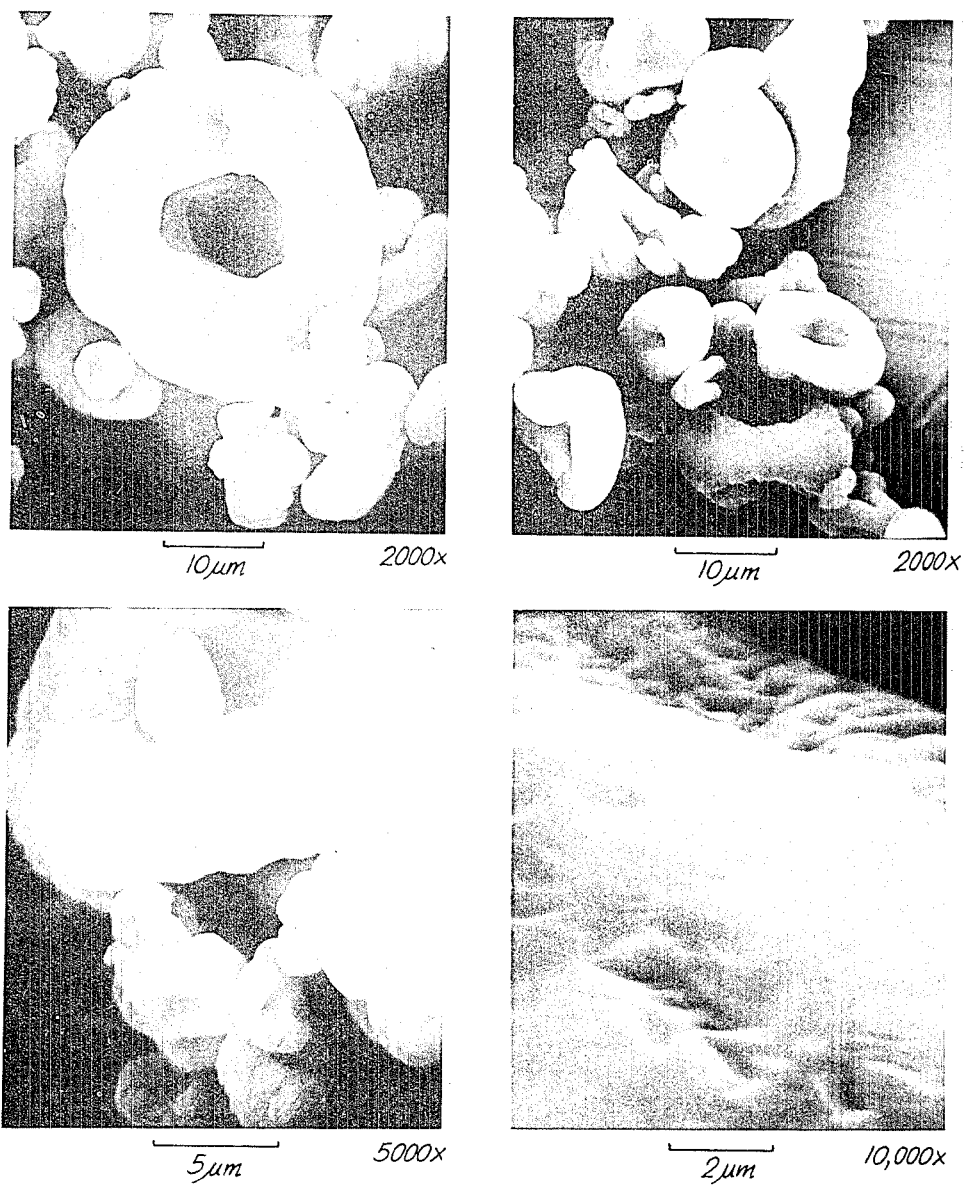
FIG. 9 shows sodium cromoglycate produced with a swirl air nozzle.
Figure 10:
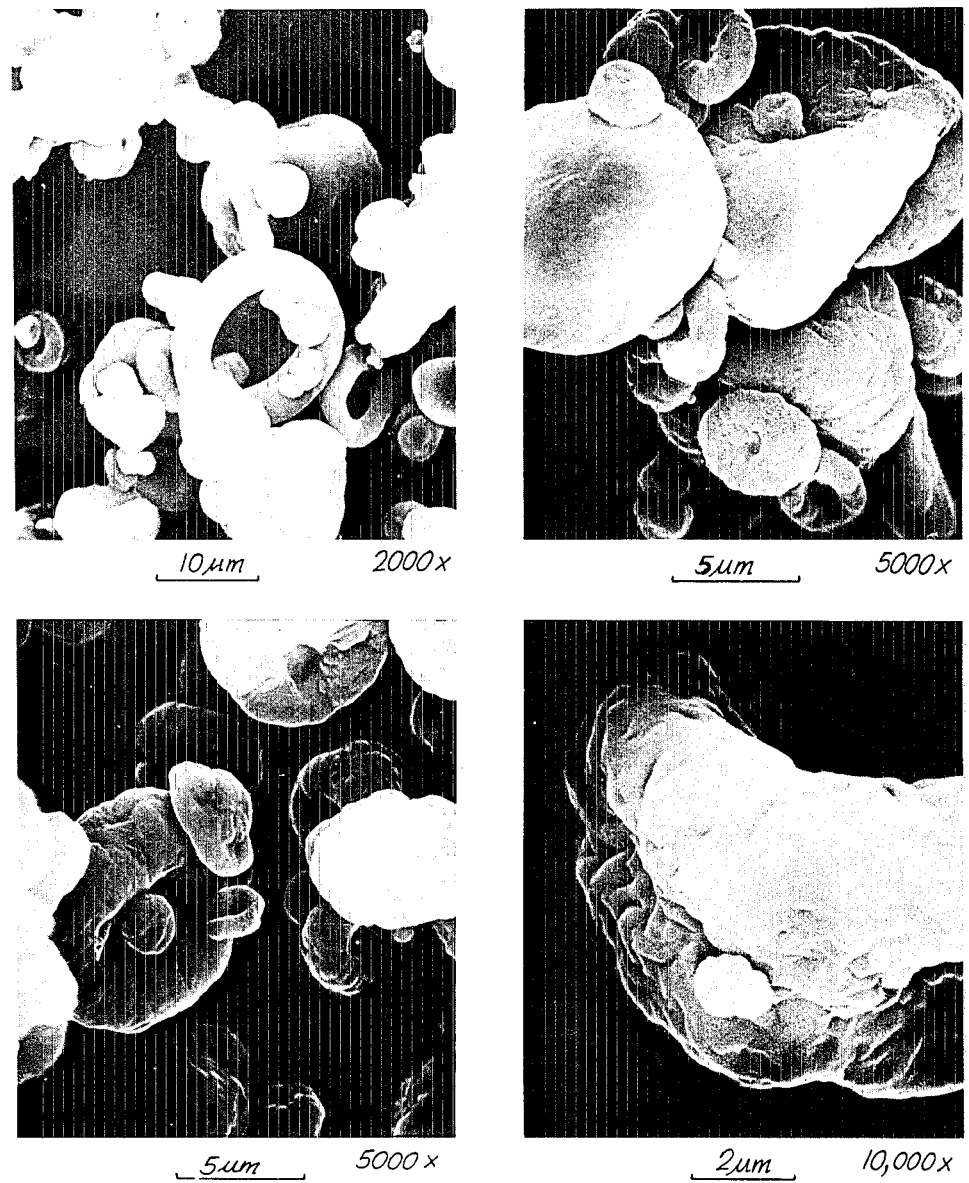
FIG. 10 shows sodium cromoglycate produced with a two fluid pressure nozzle.

The individual particles should be as rounded and smooth as possible to enable then to be carried easily in an air stream and to flow readily on capsule filling machines. We prefer the majority of the particles not to have sharp or broken edges, and for the particles themselves to be mechanically strong so that they do not break during encapsulation or on their passage from the capsule to the lung. Thus we prefer to avoid hollow shell particles. We particularly prefer a proportion of the particles, especially when the drug is sodium cromoglycate, to be toroidal in shape. In general the shape of the particles is unrelated to particle size. We have also found that in general the particles have smooth cleavage planes, are relatively non-porous and are of uniform density through each particle. With respect to their strength the particles of the present invention are strongly differentiated from the prior art soft pellets and granules, and with respect to their shape they are strongly differentiated from the prior art micronised material. A low particle density in the material is indicative of fragile particles and is, in general, to be avoided. We prefer the particles to be as uniform as possible in all respects.

The surface texture of the particles will vary according to the particular drug concerned and the techniques used to produce the particles, and can vary from a highly convoluted (brain like) structure to a random fluffy or to a smooth texture. In general we prefer to avoid highly convoluted surface textures.

The roughness of the surface of the particles can be determined by measuring the total surface area of the particle by the Brunauer, Emett and Teller (BET) method (British Standard 4359 (1969) Part 1) and comparing this with the envelope surface area of the particles as measured by permeametry (Papadakis M. (1963), Rev. Mater. Construct. Trav. 570, 79–81).

We prefer the permeametry: BET ratio to be in the range 0.5 to 1.0, preferably 0.6 to 1.0 and more preferably 0.7 to 0.97 (note a ratio of 1.0 represents a perfectly smooth particle). By way of contrast prior art micronised drugs, e.g. micronised sodium cromoglycate, have a permeametry: BET ratio of about 0.32.

We prefer the particles of the invention to be as strong and as dense as possible. The particle density of the particles (as opposed to the bulk density) may be measured by (a) the petroleum ether method in which a known weight (25 g) of powder is weighed into a measuring cylinder, a known amount of petroleum ether (50 ml) is added and the mixture shaken until all the powder is suspended. The inner walls of the measuring cylinder are washed with a small amount of petroleum ether (10 ml). Knowing the weight of powder used, the volume of petroleum ether added and the final suspension volume, the particle density can be calculated or (b) the air pycnometer method in which a given amount of powder is placed in a chamber which is hermetically sealed. The volume of the chamber is gradually reduced by a moving piston until a specified pressure is reached. The position of the piston indicates the volume of the powder particles, hence the particle density can be calculated.

We prefer the particles, e.g. of sodium cromoglycate, to have a particle density according to the above methods of from about 1.3 to 1.7 and preferably from 1.3 to 1.6 g/cm$^3$.

The micronised material, e.g. sodium cromoglycate, of the prior art has a loose bulk density of about 0.21 g/cm$^3$ and a packed bulk density of about 0.29 g/cm$^3$. In measuring loose bulk density a suitable amount of powder (40 g) is poured, at an angle of 45°, into a measuring cylinder (250 ml). The volume occupied by the powder in the measuring cylinder when related to the original mass of powder provides the measure of "loose bulk density". If the powder, in the cylinder, is tapped or jolted, e.g. using the Engelsmann Jolting Volumeter, until a stable volume is attained (500 jolts) then the lower volume after jolting when compared with the original mass of powder provides the measure of "packed bulk density".

It is also known, e.g. from British Patent Specification No. 1,549,229 that hard granules of sodium cromoglycate of particle size 60 to 200 microns (measured by sieving) can have higher bulk densities than the micronised material. However these hard granules were not designed for, and indeed would be unsuitable for, inhalation. Surprisingly we have found that the particles of the present invention have a higher bulk density than micronised material, e.g. micronised sodium cromoglycate. We prefer the particles of the present invention to have a loose bulk density of greater than about 0.3 g/cm$^3$, preferably of greater than 0.35 g/cm$^3$, more preferably of from 0.35 to 0.5 g/cm$^3$, and most preferably 0.35 to 0.4 g/cm$^3$; and a packed bulk density of from about 0.4 to 0.75 g/cm$^3$ and preferably of from 0.55 to 0.6 g/cm$^3$. The bulk densities of materials are, in general, relatively independent of the particular material used, but are dependent on the shape, size and size distribution of the particles involved.

We prefer the particles of the invention, when they comprise sodium cromoglycate and are intended for administration as a dry powder in, for example, a gelatine capsule to have a moisture content of from 5 to 14, and preferably from 8 to 11% w/w. Before filling into the capsule the powder will tend to be at the lower end of the moisture range, and after filling to be at the upper end of the range. Sodium cromoglycate powders according to the invention may also be made containing very low, e.g. less than 1%, or preferably less than 0.5%, w/w, quantities of water. These very dry powders may be used in pressurised aerosol formulations. The water contents in this specification are those measured by drying a small sample (1 to 2 g) for 15 hours at 105° C. in a vacuum oven (less than 5 mm Hg) in the presence of phosphorus pentoxide.

Examples of suitable medicaments include those used for the inhalation treatment of allergic airway diseases such as pharmaceutically acceptable salts of 1,3-bis(2-carboxychromon-5-yloxy)propan-2-ol; bronchodilators, e.g. isoprenaline, salbutamol, fenoterol, terbutaline, reproterol etc and salts of any one thereof; antibiotics, e.g. tetracycline; steroids, e.g. beclomethasone dipropionate; enzymes; vitamins and antihistamines. If desired a mixture of medicaments, for example a mixture of sodium cromoglycate and a bronchodilator, such as isoprenaline, terbutaline, fenoterol, reproterol or a salt of any one thereof, may be used. Where a highly active medicament is used which requires a small unit dose the individual particles may comprise the active ingredient together with a suitable diluent, e.g. lactose. The incorporation of the diluent in the particle avoids the possibility of segregation which is possible when individual fine particles of active ingredient are used with separate coarse particles of diluent.

We prefer that at least 50% by weight and preferably more than 90%, of the drug particles are of less than 60 microns, more preferably of less than 40 microns, most preferably of less than 20 microns and especially of less than 10 microns, e.g. less than 8 microns in diameter. We particularly prefer at least 50% of the particles to be of 2 to 6 microns in diameter. In general the smaller the mass mean diameter of the material the higher will be the dispersion of the material, as measured by the test of Example A(a).

Material according to the invention, e.g. sodium cromoglycate, having a median diameter of from 10 to 15 microns can, because of the enhanced aerodynamic properties of the particles, be equivalent in emptying and dispersion properties (see Example A) to micronised (i.e. sub 10 micron) material which has been formed into soft pellets as described in U.S. Pat. No. 4,161, 516 or blended with coarse lactose as described in U.S. Pat. No. 3,957,965.

The particle sizes in this specification are those measured with a Coulter Counter TA11 used in a standard laboratory environment, or the pipette centrifuge. In measuring particle sizes with a Coulter Counter, the sample to be analysed is dispersed in an electrolyte into which dips a glass tube. The glass tube has a 50 to 400 micron hole through the wall thereof with electrodes mounted on either side of the hole in the tube wall. The tube is immersed sufficiently for the hole and electrodes to be submerged in the liquid. The suspension is made to flow through the hole in the glass tube and as each particle passes through the orifice it displaces its own volume of electrolyte, thus changing the resistance across the hole. This change in resistance is converted into a voltage pulse with an amplitude proportional to the particle volume. The pulses are fed to an electronic counter with an adjustable threshold level such that all pulses above the threshold are counted. By setting the threshold level at different values it is possible to determine the number of particles falling within given size ranges and thus the proportion of particles in a sample which fall outside a desired particle size range. The Coulter Counter measures the volume of a sphere having the same volume as the unknown material, i.e. it measures a volume diameter.

In measuring particles by the pipette centrifuge (Christison Scientific Equipment Limited) the powder is suspended in a suitable liquid (e.g. n-butanol). The suspended sample is put in a constant speed centrifuge. Samples are withdrawn from the centrifuge at selected time intervals. The level of solids in each sample is measured (normally by drying) and the average diameter calculated using an equation derived from Stokes Law (Particle Size Measurement Published by Chapman Hall 3rd Ed. Dr. T. Allen, page 377 et seq.). The pipette centrifuge measures a mass, or Stokes, diameter.

The Coulter counter (with a 100 micron hole) is able to measure particle sizes of from about 2 to 40 microns and the pipette centrifuge is able to measure particle sizes down to about 0.2 microns.

According to the invention we also provide a process for the production of finely divided drug, which comprises atomising and drying a solution of the drug and collecting some or all of the particles which are below 60, preferably below 40, more preferably below 20 and especially below 10 microns in diameter. The particles are preferably of the sizes given above.

Spray or flash drying of materials is well established as a drying technique in the food and other industries, but is scarcely used at all in the pharmaceutical industry. Thus spray drying is routinely used in the production of coarse particle products such as dried milk, instant coffee and dextran. The use of spray drying techniques to produce very fine powders is not conventional and is unknown in the pharmaceutical field, the normal technique for producing such fine powders being to make, and then micronise, a crystalline drug. The use of a spray drying technique is advantageous in that it is adapted to suit large batch productions, thus decreasing the amount of quality control required and also in that it may remove the need for recrystalisations and micronisation to get the drug into the desired form.

Any suitable form of atomiser can be used. Atomisation results from an energy source acting on liquid bulk. Resultant forces build up to a point where liquid break-up and disintegration occurs and individual spray droplets are created. The different atomisation techniques available concern the different energy forms applied to the liquid bulk. Common to all atomisers is the use of energy to break-up liquid bulk. Centrifugal, pressure and kinetic energy are used in common forms of atomiser. Sonic and vibratory atomisers are also used. Specific atomisers which may be mentioned include rotary atomisers, e.g. those involving vaned wheels, vaneless discs, cups, bowls and plates; pressure atomisers, e.g. those involving pressure nozzles, centrifugal pressure nozzles, swirl chambers and grooved cores; kinetic energy or pneumatic atomisers, e.g. those involving two or three fluids, or internal or external mixing; and sonic energy nozzles, e.g. involving sirens or whistles. We prefer to use kinetic or pneumatic energy atomisers particularly two fluid pressure or syphon or sonic nozzle atomisers. In general two fluid pressure nozzles tend to produce powders having more desirable characteristics than two fluid syphon nozzles and two fluid pressure nozzles also tend to give more reproducible results and use less energy.

The atomiser can be used in a spray or flash drying apparatus.

The conditions of operation of the apparatus and storage of the solution (e.g. pH and temperature) should clearly not be such as to degrade the drug, or introduce impurities, or biological contamination, into the drug.

The spray drying apparatus preferably comprises the atomiser, a main chamber, one or more (e.g. two) cyclones, a bag filter and, if desired or necessary to maximise recovery, a terminal wet scrubber or electrostatic precipitator. The particle collection system is designed to capture the desired size range of particles and also to maximise the yield. All over and under size material may be recovered and recycled or put to other uses.

The solution of the drug may be in any suitable solvent, e.g. water for a water soluble drug. The concentration of the drug in the solvent may vary over a wide range, e.g. in the case of sodium cromoglycate from 1 to 25, preferably 5 to 20, and especially 10 to 15% w/v. In general we prefer to use a high concentration of drug as the volume and energy requirements of the atomisation and drying process are thereby diminished. To avoid possible blockage of the atomisation device and to avoid the incorporation of unwanted impurities it is desirable to filter the solution immediately before it is passed to the atomiser. The particle size of the product tends to increase with concentration, but not rapidly, and in general concentration is not controlling with respect to particle size.

The temperature of the air inlet and outlet to the spray drier main chamber may vary over a wide range (the range being dependent on the product being dried, the solution through put and the final moisture content required) and suitable temperatures may be found to suit each drug and solvent by simple routine experiment. In the case of aqueous solutions (of for example sodium cromoglycate), we have found that an air inlet temperature of from 160° to 350° C., preferably from 180° to 230° C., and an outlet temperature of from 70° to 250° C. and preferably of from 70° to 120° C. are suitable.

The temperature of the solution to be fed to the spray drier will vary with the drug and the solvent to be used. In general we prefer to use a temperature at which the solution can be stored for a long period in large batches without degradation. As high a temperature as possible comensurate with stability is desirable to reduce solution viscocity and provide energy to the drying process.

The air flow rate, direction into the spray drier, the temperature of the air and the rate of feed of solution to the spray drier can be optimised by simple experiment. All of the parameters in the spray drying process interrelate and can be adjusted to produce the desired product.

Gases other than air, e.g. nitrogen, can be used if desired. The use of an inert gas will be advantageous when an inflamable solvent or a readily oxidisable drug is used. The gas used, e.g. air or nitrogen, may, if desired, be recycled to avoid loss of entrained drug and/or to conserve energy and the inert gas.

The particle size of the product will be set by the concentration of the feed solution, the rate of feed to the spray drier, the means of atomising the solution, e.g. the type of atomiser and the pressure of the air, and solution to be dried, the temperature and temperature gradient within the drier and, to a small extent, the air flow in the drier. The particle size and air flow will then dictate where the desired product is collected and the means of collection.

The particle size of the product tends to remain fairly constant with liquid flow rate through the atomiser, but to decrease with increasing air pressure up to a limiting pressure, e.g. of about 11Kg $cm^{-2}$. The range of air pressures suitable will naturally depend on the atomisation device used, but we have found that air pressures of from about 2 Kg $cm^{-2}$ to 11KG $cm^{-2}$ are in general effective, e.g. with a 0.4 mm orifice syphon two fluid nozzle. In order to achieve reproducible results we prefer to maintain a constant air flow to the dryer and appropriate air flow control devices may be used if desired.

The cyclone or cyclones used to collect the dried particles are of conventional design, but adapted to collect finer particles than is normal. Thus the pressure differential across the cyclones, the combination of two or more cyclones and the design of the particular cyclones used may be adjusted to enable capture of the fine particles. The bag filter used to collect the finest material is of conventional design and is readily available. The filter medium within the bag filter preferably has a high capture efficiency for particles of approximately 0.5 microns in diameter and greater. A particularly suitable medium is a polytetrafluoroethylene membrane supported on a polypropylene or polyester cloth, e.g. a needle felt cloth. Any electrostatic precipitator, or wet scrubber, used will also be of conventional design.

The product may be classified, e.g. sieved or air classified, to remove over and under sized material. The over and under sized material may be recycled or used for other purposes.

The final product may be put up in any suitable form of container such as a capsule or cartridge. Where it is desired to use the product in association with other ingredients such as colourants, sweeteners or carriers such as lactose, these other ingredients may be admixed with the particles of the invention using conventional techniques or may be incorporated in the solution to be spray dried. We prefer the particles of the invention to contain medicament and water only. Mixtures of two or more different particles according to the invention, e.g. of sodium cromoglycate and a bronchodilator, such as isoprenaline sulphate or terbutaline sulphate, may be made and filled into suitable containers.

According to our invention we also provide a method of application of a medicament, e.g. sodium cromoglycate, to a patient by way of inhalation, the medicament being dispersed into an air stream, characterised in that an opened, e.g. pierced, container, e.g. capsule, containing particles according to the invention is rotated and vibrated in an air stream which is inhaled by the patient. The rotation and vibration may conveniently be produced by any one of a number of devices, e.g. the device of British Patent Specification No. 1,122,284.

The particles according to the invention may also be used in pressurised aerosol formulations (together with propellant gases, e.g. a mixture of two or more of propellants 11, 12 and 114, preferably with a surface active agent, e.g. sorbitan trioleate) or may be formed into soft pellets, e.g. as described in U.S. Pat. No. 4,161,516, or may be used for application to the skin. Sodium cromoglycate is known to be of use in the treatment of a wide variety of conditions, e.g. asthma and hay fever.

From another aspect the invention also provides a capsule, cartridge or like container containing particles according to the invention, optionally in association with other particles. We prefer the container to be loosely filled to less than about 80% by volume, preferably less than about 50% by volume, with the particles of the invention. The particles are preferably not compacted into the container. We prefer the container, e.g. capsule, to contain from 10 to 100 mg, e.g. about 20 mg, of the particles.

The invention will now be illustrated by the following Examples in which all parts and percentages are by weight unless otherwise stated.

EXAMPLE 1

The active compound (A) was dissolved in a solvent, normally water, to a concentration B (% w/v). This solution flowed under pressure or vacuum to the atomiser. At the atomiser the solution temperature was normally greater than 50° C. Conditions of atomisation (C) and of droplet drying (D) were preset and remained constant throughout the run. The powder was captured in the drying chamber, in two cyclones (firstly a Vantongeren Buell AC 130 cyclone of diameter 22 cm and height 74 cm and secondly a high efficiency Stairmand formula cyclone of diameter 14 cm) and finally in a bag filter which had as the filter media polytetrafluoroethylene lined polypropylene. At the end of each run the contents of each collection vessel was weighed (E) and sized(F) (Coulter Counter Model TA11).

(a) Varying Active Ingredients

Using a concentration (B) of 10% w/v in water, and atomisation conditions (C) a pressure two fluid nozzle 0.4 mm orifice), a solution flow rate of 65 ml $min^{-1}$ and an atomisation pressure of $27\times10^3$ Kg $m^{-2}$ the results shown in Table 1 were obtained.

*Note*—Electron micrographs (see FIGS. 1 to 4) showed

Salbutamol Sulphate—smooth spheres
Terbutalene Sulphate—"orange peel" spheres
Isoprenaline Sulphate—smooth spheres 4,6-Dioxo-10-propyl-4H,6H-pyrano[3,2-g]pyran-2,8-dicarboxylic acid disodium salt "orange peel" spheres with surface cracks

| Sodium Cromoglycate Sodium Cromoglycate/ other active ingredients | "doughnut", spheres and collapsed spheres. |
| --- | --- |

(b) Varying Atomisation Techniques

Active ingredient (A)—Sodium Cromoglycate. Conditions used and results obtained are given in Tables 2 and 2a.
Two fluid syphon nozzle—CT (London) Ltd. CT Type J1A 16/50 (4 mm orifice)
Two fluid pressure nozzle—CT (London) Ltd. CT Type J11
Ultrasonic nozzle—Ultrasonics Ltd, 035 H Sonicore nozzle
Swirl Air nozzle—Delevan Ltd—Swirl Air Nozzle Type 32163-1.

(c) Variation of Powder Collection Techniques

The powder is collected in the drying chamber, cyclones and a bag filter.
Active ingredient A—Sodium Cromoglycate.
Conditions used and results obtained are given in Tables 3 and 3a.

Powder Capture Equipment

Main chamber (MC) size—13 cu ft (give metric equivalent)
Cyclone A—Stairmand High Efficiency Cyclone (Diameter 14 cm)
Cyclone B—Vantogeren Buell AC 130 Cyclone (Diameter 22 cm, Height 74 cm)
Cyclone C—Stairmand High Efficiency Cyclone (Diameter 11.9 cm)
Bag Filter (BF)—1.86 $M^2$ polytetrafluoro ethylene lined polyester.

(d) Variation of Droplet Drying Time

Droplet drying time is dependent upon both the temperatures used in drying, i.e. air inlet temperature, the residence time in the drying chamber (normally this is as a result of drying chamber size) and level of evaporation required. Residence time can be changed by modifying the drying air flow rate but this results in a significant change in efficiency of capture within the latter cyclones. Table 4 indicates the range of drying conditions used. Increased residence time (i.e. slower drying) produces improved particles with improved performance.

Figure 11:
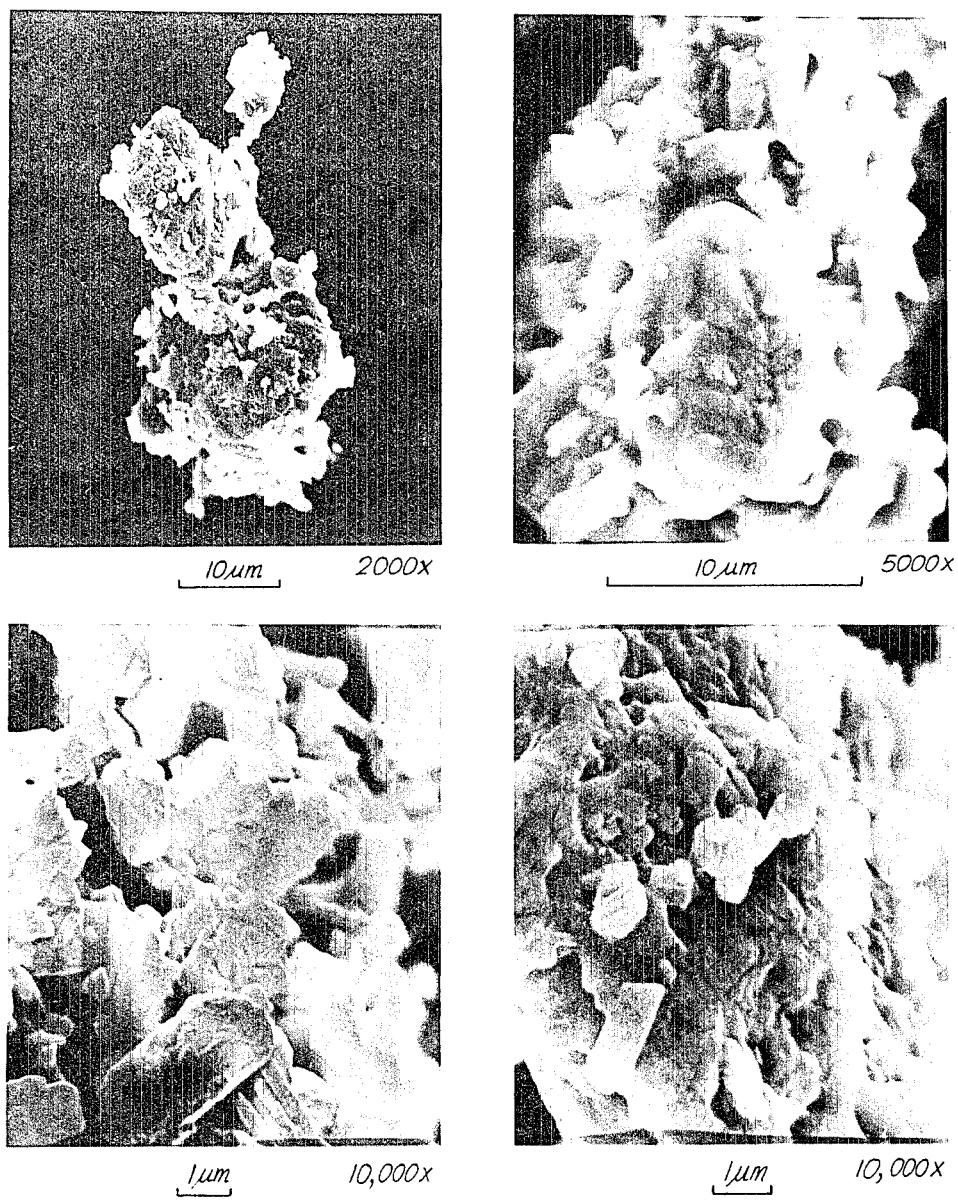
FIG. 11 shows conventional pelletized sodium cromoglycate.
Figure 12:
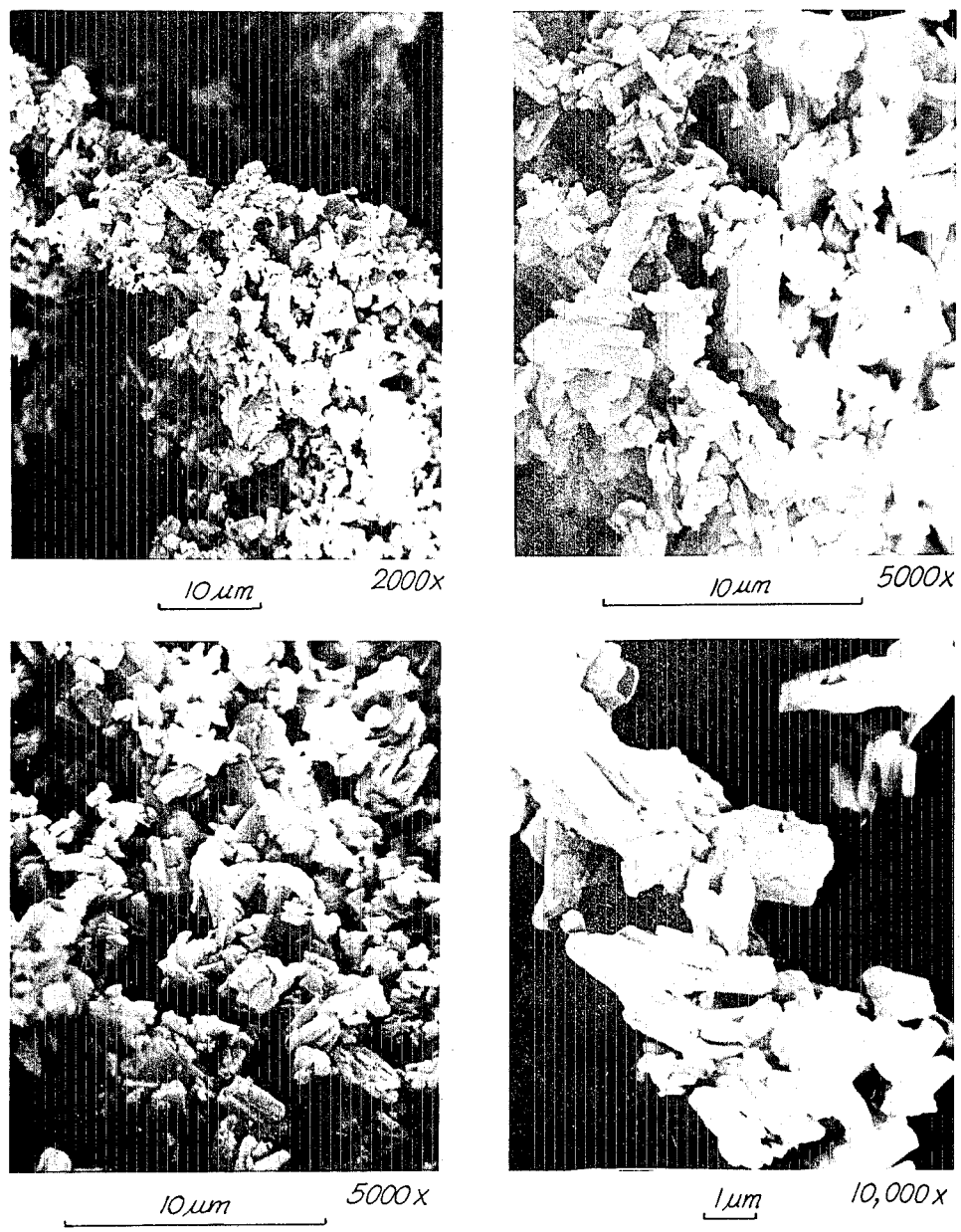
FIG. 12 shows conventional micronised sodium cromoglycate.

Electron micrographs of a selection of the above powders are shown in the accompanying Figures. FIGS. 11 and 12 are electron micrographs of, respectively pelletised sodium cromoglycate, and micronised sodium cromoglycate and are included for comparison purposes only. In each of FIGS. 1 to 12 the magnification and an approximate scale is given.

TABLE 1

| RUN NO. | ACTIVE INGREDIENT (A) | DRYING CONDITIONS (D) | | | | POWDER RECOVERED E/F | | ELECTRON MICROGRAPH FIG. No |
| --- | --- | --- | --- | --- | --- | --- | --- | --- |
| | | INLET TEMP. °C. | OUTLET TEMP. °C. | AIR FLOW RATE $m^3s^{-1}$ | MAIN CHAMBER | CYCLONE B micron median | CYCLONE A volume diameter | |
| 1. | Sodium Cromoglycate | 195 | 100 | 0.034 | 2.0/— | 80/7.5 | 18/3.4 | |
| 2. | Terbutalene Sulphate | 202 | 102 | " | —/— | 83/4.3 | 17/4.0 | 1 (B cyclone) |
| 3. | Salbutamol Sulphate | 204 | 105 | " | —/— | 78/4.1 | 22/2.7 | |
| 4. | Isoprenaline Sulphate | 201 | 100 | " | 33/— | 34/6.5 | 33/3.3 | |
| 5. | 4,6-Dioxo-10-propyl-4H,6H—pyrano}3,2-g pyran-2,8-dicarboxylic acid disodium salt | 200 | 100 | " | 7/16.5 | 78/6.2 | 15/4.1 | 2 (B cyclone) |
| 6. | Sodium Cromoglycate (100)/ Terbutalene Sulphate (0.522) w/w | 200 | 101 | " | 8/— | 75/6.6 | 17/3.6 | 3 |
| 7. | Sodium Cromoglycate (100)/ Sulbutamol Sulphate (0.522) w/w | 220 | 88 | " | 17/— | 58/7.4 | 25/4.2 | |
| 8. | Sodium Cromoglycate (100)/ Isoprenaline Sulphate (0.522) w/w | 205 | 106 | " | 13/19.0 | 75/7.0 | 12/3.2 | 4 |
| 9. | Salbutamol Sulphate* (1.6)/ Lactose (100) w/w | 200 | 100 | " | 7/— | | 93/7.8 (cyclone C) | |

*Cyclone configuration changed to MC/C/BF.

TABLE 2

| RUN NO. | ATOMISER TYPE | ATOMISATION CONDITIONS (C) | | | DRYING CONDITIONS (D) | | | |
| --- | --- | --- | --- | --- | --- | --- | --- | --- |
| | | SOLUTION CONC % w/v | SOLUTION FEED RATE $Ls^{-1} \times 10^{-3}$ | ATOMISATION PRESSURE $Kgm^{-2} \times 10^3$ | INLET TEMP. °C. | OUTLET TEMP. °C. | AIR FLOW RATE $m^3s^{-1}$ | MAIN CHAMBER |
| 10. | SLOTTED DISC | 10 | 0.57 | 23000 rpm | 220 | 134 | 0.034 | * |
| 11. | SLOTTED DISC | 10 | 0.48 | | 214 | 130 | " | 20/— |

TABLE 2-continued

| | | | | | | | | | |
|---|---|---|---|---|---|---|---|---|---|
| 12. | HOLED DISC | 10 | 0.70 | | 220 | 118 | " | | 32/— |
| 13. | INVERTED CUP | 10 | 0.50 | | 215 | 127 | " | | 21/24 |
| 14. | TWO FLUID SYPHON | 5 | 0.33 | 150.7 | 238 | 125 | | 0.034 | 1/— |
| 15. | NOZZLE | 20 | 1.33 | 150.7 | 205 | 94 | " | | 26/15.5 |
| 16. | | 10 | 0.90 | 56.4 | 210 | 108 | " | | 7/— |
| 17. | | 10 | 0.63 | 105.7 | 225 | 113 | " | | 5/— |
| 18. | TWO FLUID | 15 | 0.37 | 28.2 | 190 | 132 | | 0.034 | 8/29 |
| 19. | PRESSURE | 10 | 0.33 | 28.2 | 200 | 95 | " | | 12/— |
| 20. | NOZZLE | 10 | 1.52 | 18.3 | 210 | 104 | " | | 24/— |
| 21. | 4 mm orifice | 10 | 0.42 | 39.5 | 203 | 137 | " | | 5/25 |
| 22. | TWO FLUID | 10 | 1.33 | 36.6 | 205 | 95 | | 0.034 | 13/— |
| 23. | PRESSURE NOZZLE 5 mm orifice | 10 | 1.17 | 21.1 | 205 | 90 | " | | 12/— |
| 24. | ULTRASONIC NOZZLE | 10 | 1.47 | 35.2 | 210 | 87 | | 0.034 | 6/— |
| 25. | SWIRL AIR NOZZLE | 15 | 1.17 | 49.3 | 200 | 90 | | 0.034 | 13/— |

| | | POWDER RECOVERED E/F | | | |
|---|---|---|---|---|---|
| RUN NO. | ATOMISER TYPE | CYCLONE B micron median | CYCLONE A volume diameter | BAG FILTER | ELECTRON MICROGRAPH FIG. No |
| 10. | SLOTTED DISC | 91/15 | 9/5.2 | | 5 (B cyclone) |
| 11. | SLOTTED DISC | 78/22 | 2/4.0 | | 6 (B cyclone) |
| 12. | HOLED DISC | 65/17 | 3/4.3 | | |
| 13. | INVERTED CUP | 79/17.7 | | | |
| 14. | TWO FLUID SYPHON | 19/4.5 | 31/2.8 | 49/— | |
| 15. | NOZZLE | 12/7.4 | 62/3.1 | | |
| 16. | | 70/8.5 | 23/3.0 | | |
| 17. | | 34/4.7 | 31/2.9 | 30/2.1 | |
| 18. | TWO FLUID | 62/6.8 | 30/3.7 | 9.3/0 | 7 (A cyclone) |
| 19. | PRESSURE | 77/9.2 | 11/3.5 | | |
| 20. | NOZZLE | 74/16.0 | 2/4.0 | | |
| 21. | 4 mm orifice | 53/10 | 33/3.4 | | |
| 22. | TWO FLUID | 77/10.5 | 10/3.2 | | |
| 23. | PRESSURE NOZZLE 5 mm orifice | 79/9.2 | 9/4.2 | | |
| 24. | ULTRASONIC NOZZLE | 82/9.6 | 12/3.3 | | 8 |
| 25. | SWIRL AIR NOZZLE | 79/14.5 | | 8/— | 9 |

*Chamber contents showed incomplete drying.

TABLE 2A

| Run No. | Dispersion (see Example Ac) % w/w | Coulter particle size volume median diameter | Particle Density g/cm³ | | Bulk Density g/cm³ | | Moisture % w/w | Emptying (see Example Ab) % | BET | Permeametry m²kg⁻¹ × 10³ | Permeametry BET ratio |
|---|---|---|---|---|---|---|---|---|---|---|---|
| | | | Air Pycnometer | Petroleum Ether | Loose | Packed | | | | | |
| 10. | 12.6 | 15 | — | — | — | — | — | 86 | — | — | — |
| 10. | 41.4 | 5.2 | — | — | — | — | — | 80 | — | — | — |
| 11. | — | 22. | 1.35 | 1.45 | 0.42 | 0.58 | 7.0 | — | 0.62 | 0.496 | 0.79 |
| 12. | — | 17 | — | — | 0.43 | 0.63 | — | 88 | — | — | — |
| 12. | 40.0 | 4.3 | — | — | — | — | — | 55 | — | — | — |
| 13. | — | 17.7 | 1.56 | — | 0.50 | 0.74 | 5.5 | 88 | 0.48 | 0.33 | 0.69 |
| 14. | — | 2.9 | — | — | — | — | — | 57 | — | — | — |
| 15. | 8.6 | 15.5 | — | — | — | — | — | 93 | — | — | — |
| 17. | 21.4 | 2.8 | 1.59 | 1.66 | 0.34 | 0.48 | 8.5 | 59.2 | 2.42 | 1.25 | 0.52 |
| 20. | — | 24 | 1.33 | 1.45 | — | — | — | 98 | — | — | — |
| 23. | 19.6 | 9.2 | — | — | — | — | — | 92 | — | — | — |
| 23. | 26.1 | 4.2 | 1.56 | 1.55 | 0.31 | 0.43 | — | 28 | 1.75 | 1.1 | 0.63 |
| 24. | 12.3 | 14.5 | — | — | — | — | 6.9 | 96.3 | — | — | — |
| 25. | 24.4 | 9.5 | — | — | — | — | — | 96 | — | — | — |

TABLE 3

| RUN | POWDER CAPTURE EQUIPMENT | ATOMISATION CONDITIONS (C) | | | | DRYING CONDITIONS (D) | | |
|---|---|---|---|---|---|---|---|---|
| | | ATOMISER | SOLUTION CONC | SOLUTION FEED RATE | ATOMISATION PRESSURE | INLET TEMP. | OUTLET TEMP. | AIR FLOW RATE |

TABLE 3-continued

| NO. | CONFIGURATION | TYPE | % w/v | Ls$^{-1}$ × 10$^{-3}$ | Kgm$^{-2}$ × 10$^3$ | °C. | °C. | m$^3$s$^{-1}$ |
|---|---|---|---|---|---|---|---|---|
| 26. | MC/A/B/BF | TWO FLUID SYPHON NOZZLE | 10 | 1.17 | 105.7 | 210 | 95 | 0.034 |
| 27. | MC/BF | TWO FLUID SYPHON NOZZLE | 10 | 1.27 | 105.7 | 215 | 98 | 0.034 |
| 28. | MC/B/A/BF | TWO FLUID SYPHON NOZZLE | 10 | 0.88 | 105.7 | 218 | 112 | 0.034 |
| 29. | MC/BF | TWO FLUID PRESSURE NOZZLE 4 mm | 10 | 1.5 | 18.3 | 180 | 80 | 0.034 |
| 30. | MC/BF | | 10 | 0.42 | 33.8 | 190 | 120 | 0.034 |
| 31. | MC/B/A/BF | ORIFICE | 10 | 1.52 | 18.3 | 210 | 104 | 0.034 |
| 32. | MC/C/BF | | 10 | 0.9 | 35.2 | 195 | 95 | 0.034 |
| 33. | MC/BF | TWO FLUID PRESSURE NOZZLE 5 mm | 10 | 1.73 | 16.2 | 185 | 74 | 0.034 |
| 34. | MC/B/A/BF | | 10 | 1.16 | 21.1 | 205 | 90 | 0.034 |
| 35. | MC/C/BF | ORIFICE | 15 | 1.23 | 26.8 | 222 | 102 | 0.034 |

| RUN NO. | POWDER CAPTURE EQUIPMENT CONFIGURATION | DRYING CONDITIONS (D) MAIN CHAMBER | POWDER RECOVERED (E/F) | | | BAG FILTER |
|---|---|---|---|---|---|---|
| | | | CYCLONE A median | CYCLONE B volume diameter | CYCLONE C microns | |
| 26. | MC/A/B/BF | 3/— | 87/9.6 | 10/4.2 | | |
| 27. | MC/BF | 14/17 | | | | 86/5.2 |
| 28. | MC/B/A/BF | 3/— | 40/2.9 | 35/6.4 | | 22/2.0 |
| 29. | MC/BF | 50/— | | | | 50/13.5 |
| 30. | MC/BF | 4/23 | | | | 96/5.2 |
| 31. | MC/B/A/BF | 24/— | 3/4.0 | 73/16 | | |
| 32. | MC/C/BF | 11/— | | | 86/6.5 | 3/— |
| 33. | MC/BF | 61/— | | | | 39/14 |
| 34. | MC/B/A/BF | 12/— | 9/4.2 | 79/9.2 | | |
| 35. | MC/C/BF | 16/— | | | 86/11.5 | |

TABLE 3a

| Run No. | Dispersion (see Example Ac) % w/w | Pipette Centrifuge particle size mass median diameter | Coulter particle size volume median diameter | Particle Density g/cm$^3$ Air Pycnometer | Particle Density g/cm$^3$ Petroleum Ether | Bulk Density g/cm$^3$ Loose | Bulk Density g/cm$^3$ Packed | Moisture % w/w | Emptying (see Example Ab) % | BET | Permeametry m$^2$kg$^{-1}$ × 10$^3$ | Permeametry BET ratio |
|---|---|---|---|---|---|---|---|---|---|---|---|---|
| 26. | 25.4 | — | 4.2 | — | — | — | — | — | 91 | — | — | — |
| 27. | 8.3 | — | 17.0 | — | — | — | — | — | 95 | — | — | — |
| 28. | — | 1.7 | 2.0 | — | — | — | — | — | 95 | — | — | — |
| 29. | 17.1 | — | 13.5 | — | — | — | — | — | 97 | — | — | — |
| 31. | — | — | 24.0 | 1.33 | 1.45 | — | — | — | 98 | — | — | — |
| 32. | 20.6 | — | 8.5 | — | — | — | — | — | 93 | — | — | — |
| 33. | 20.0 | — | 14.0 | — | — | — | — | — | 97 | — | — | — |
| 34. | 19.6 | — | 9.2 | — | — | — | — | — | 92 | — | — | — |
| | 26.1 | — | 4.2 | 1.56 | 4.55 | 0.31 | 0.43 | — | 98 | 1.75 | 1.12 | 0.64 |
| 35. | 20.9 | — | 11.5 | — | — | — | — | 8.1 | 92.9 | — | — | — |

TABLE 4

| RUN NO. | ATOMISER TYPE | ATOMISATION CONDITIONS | | | DRYING CONDITIONS | | | ELECTRON MICROGRAPH FIG. |
|---|---|---|---|---|---|---|---|---|
| | | SOLUTION CONC. % w/v | SOLUTION FEED RATE Ls$^{-1}$ × 10$^{-3}$ | ATOMISATION PRESSURE Kgm$^{-2}$ × 10$^3$ | INLET TEMP. °C. | OUTLET TEMP. °C. | AIR FLOW RATE m$^3$s$^{-1}$ | |
| 36. | Two Fluid Syphone Nozzle | 20 | 1.67 | 176.2 | 165 | 88 | 0.034 | |
| 37. | | 5 | 0.48 | 55.0 | 345 | 254 | 0.034 | |
| 38. | Two Fluid Pressure Nozzle 4 mm | 10 | 0.67 | 35.2 | 305 | 122 | 0.034 | 10 (1st cyclone) |
| 39. | Orifice | 10 | 1.28 | 23.3 | 140 | 60 | 0.034 | |

EXAMPLE 2

The experiment was carried out using a spray drier which had a main chamber and a single cyclone. (Main chamber 0.37 m$^3$, cyclone Stairmand High Efficiency design with diameter 119 mm). Atomisation was achieved using a two fluid pressure nozzle with orifice diameter 0.44 mm. With an aqueous sodium cromoglycate feed solution concentration of 15% w/v, an air flow rate of 0.034 $M^3s^{-1}$ and other conditions set out in Table 5, the results shown in Tables 5, 5a and 5b were obtained. Table 5b gives test results when the powders produced according to this Example have been filled into hard gelatine capsules.

The powder was satisfactory in the capsule emptying test.

The appearance of the powder under the light microscope was of uniform spheres or collapsed spheres with negligible fractured particles.

EXAMPLE A

TABLE 5

| | ATOMISATION CONDITIONS (C) | | DRYING CONDITIONS (D) | | POWDER RECOVERED E/F | |
| --- | --- | --- | --- | --- | --- | --- |
| | | | | | MAIN | |
| | SOLUTION FEED | ATOMISATION | INLET | OUTLET | CHAMBER | CYCLONE |
| RUN | RATE | PRESSURE | TEMP | TEMP | %/Micron | Volume Median |
| NO. | $Ls^{-1} \times 10^{-3}$ | $Kgm^{-2} \times 10^3$ | °C. | °C. | | Diameter |
| 40. | 1.33 | 27.5 | 190–200 | 70–80 | 33/— | 67/13.0 |
| 41. | 1.58 | 21.1 | 220–230 | 85–95 | 40/— | 60/14.7 |
| 42. | 1.43 | 25.4 | 195–200 | 80–90 | 20/— | 80/13.8 |
| 43. | 1.50 | 24.0 | 195–204 | 75–85 | 33/— | 67/13.7 |
| 44. | 1.58 | 22.6 | 190–200 | 70–80 | 36/— | 64/14.0 |
| 45. | 1.50 | 24.0 | 195–205 | 80–90 | 34/— | 66/16.5 |

TABLE 5a

| | POWDER DATA | | | | | |
| --- | --- | --- | --- | --- | --- | --- |
| | RUN NUMBER | | | | | |
| TEST | 40 | 41 | 42 | 43 | 44 | 45 |
| Moisture % w/w | 8.8 | 9.7 | 8.4 | 9.8 | 9.8 | 9.5 |
| Particle Size: | | | | | | |
| Volume median diameter microns | 13.0 | 14.7 | 13.8 | 13.7 | 14.0 | 16.5 |
| % w/w 6 microns | 10 | 8 | 9 | 8 | 8 | 7 |
| % w/w 30 microns | 4 | 7 | 8 | 8 | 8 | 15 |
| Loose Bulk Density $g/cm^3$ | 0.39 | 0.38 | 0.39 | 0.38 | 0.36 | 0.37 |
| Packed Bulk Density $g/cm^3$ | 0.58 | 0.56 | 0.58 | 0.57 | 0.57 | 0.59 |

The drug is dispensed from a gelatine capsule 6.4 mm in diameter and having two holes 0.8 mm in diameter in a shoulder thereof mounted in a device (commercially available under the Registered Trade Mark 'Spinhaler') according to British Pat. No. 1,122,284 having a drawn wire shaft 2.03 mm diameter journalled in a hard nylon bearing tube 13 mm long and having an internal diameter of 2.08 mm at its inner end (i.e. that end housing the free end of the shaft) and of 2.44 mm at its other end.

The particles are preferably such that when put up in gelatine capsules 6.4 mm in diameter each containing 20 mg of the particles they meet the criteria set out in the tests below:

(a) Dispersion test

TABLE 5b

| | CAPSULE DATA | | | | | |
| --- | --- | --- | --- | --- | --- | --- |
| | RUN NUMBER | | | | | |
| TEST | 40 | 41 | 42 | 43 | 44 | 45 |
| Moisture Content % w/w | | | | | | |
| Powder when in the capsule | 12.1 | 11.9 | 12.2 | 12.2 | 13.3 | 13.2 |
| Capsule shell | 13.9 | 14.2 | 13.3 | 13.5 | 13.1 | 13.0 |
| Total mg/capsule | 11.8 | 11.9 | 11.9 | 11.6 | 11.6 | 11.5 |
| Emptying Test % w/w (See Example Ab) | | | | | | |
| Mean | 95.4 | 96.4 | 97.1 | 97.2 | 97.4 | 96.2 |
| Range | 87.3–99.1 | 92.6–99.3 | 93.1–100 | 95.5–98.9 | 92.7–100 | 94.3–98.2 |
| Dispersion mg/capsule (See Example Ac) | 5.32 | 4.03 | 4.74 | 4.97 | 4.28 | 3.12 |

EXAMPLE 3

Pressure Nozzle

The trial was carried out using a spray drier having a main chamber and a single cyclone.

This experiment was used to demonstrate that the pressure nozzle was capable of providing small particles and establishing the order of magnitude of pressure required to produce particles with an average mass mean diameter of less than 10 microns. An atomiser pressure of $2.1 \times 10^6$ $Kgm^{-2}$, a feed concentration of 6% w/v of aqueous sodium cromoglycate, an air inlet temperature of 230° C. and an air outlet temperature of 120° C. was used. The resulting powder had particles of size 11 microns mass mean diameter with a particle bulk density similar to that of micronised powder, but with a tapped bulk density twice that of micronised powder.

The filled capsules are mounted in the capsule holder of the powder insufflator (having the specific dimensions set out immediately above) of British Patent Specification No. 1,122,284 and pierced to produce two holes of 0.8 mm diameter in a shoulder of the capsule. The dispersion of the medicament in the cloud delivered by the insufflator is determined using a modified version of the multistage liquid impinger described in British Patent Specification No. 1,081,881. The modifications incorporated in the present design are the addition of an extra impingement stage, and of a glass tube with a right angled bend approximately mid-way along its length. The extra impingement stage was added prior to the three stages described in British Patent Specification No. 1,081,881 and consists essentially of a jet of internal diameter 2.5 cm and a collection plate of diameter 5 cm designed to give an effective cut-off of approximately 12 microns at an air flow rate of 60 liters per minute.

The glass tube, also of internal diameter 2.5 cm abutts the external end of the jet of the extra stage. The insufflator is inserted into the upper, horizontal end of the glass tube and air drawn through at 60 liters per minute for 30 seconds. At least five capsules are treated in this manner and the results are averaged. The weight of the medicament collected on each stage of the impinger, on the glass tube, and on a filter paper positioned after the final stage is determined spectrophotometrically after solution in an appropriate volume of distilled water (or by any other appropriate method).

The particles disperse satisfactorily if an average total for each capsule of at least 0.5 mg, preferably at least 2.5 mg and most preferably at least 5.0 mg of the particles are found on a combination of the last two stages and filter paper of the multi-stage liquid impinger.

(b) Emptying test

The filled capsules are mounted in the capsule holder of the powder insufflator (having the specific dimensions set out above) of British Patent Specification No. 1,122,284 and pierced to produce two holes of 0.8 mm diameter in a shoulder of the capsule. The insufflator is placed in a device adapted to suck air through it for 2.5 seconds, the air flow rate at no time exceeding 60 liters per minute, and being held at 60 liters per minute for at least 2 seconds. The capsule mounted in the insufflator is subjected to 4 sucks as described and the weight of the material remaining in the capsule is determined. The above procedure is repeated 20 times and the average of the results determined.

The capsules empty satisfactorily if an average of at least 50%, preferably at least 75% and most preferably at least 90% by weight of the material has emptied from each capsule.

(c) Dispersion

Single Stage Impinger

In a further refinement, the multistage liquid impinger of Example A(a) was simplified to give a single stage liquid impinger, consisting of a single impingement assembly with a filter downstream. The impingement assembly consisted of a vertical jet of internal diameter 1.9 cm and a collection plate of diameter 3.8 cm. At the upper end, the jet was bent through an angle of 90° and the insufflator was attached to the distal end of this horizontal portion. The impingement characteristics of this single stage device were intended to be such that material reaching the filter of this device were similar in particle size to that reaching the final two stages and filter of the multistage liquid impinger of Example A(a). The percentage of material reaching the filter of the device is determined.

In all samples of sodium cromoglycate prepared by the techniques exemplified above at least some of the particles were of toroidal (ring doughnut) shape.

We claim:

1. A capsule, cartridge, or aerosol container containing an inhalation drug for the treatment of allergic airway disease, said drug consisting essentially of spray-dried sodium cromoglycate in finely divided and unagglomerated form, wherein a substantial proportion of the individual drug particles have a ring doughnut shape, at least 50% by weight of said particles having diameters less than 60 microns.

2. A capsule, cartridge or container in accordance with claim 1, wherein said inhalation drug has a permeametry:BET ratio in the range of 0.5 to 1.0.

3. A capsule, cartidge or container in accordance with claim 1 wherein the particle density of said drug is 1.3 to 1.7 g/cm$^3$.

4. A capsule, cartridge or container in accordance with claim 1 wherein said drug has a loose bulk density of greater than 0.3 g/cm$^3$.

5. A capsule, cartridge or container in accordance with claim 1 wherein said drug has a packed bulk density of 0.4 to 0.75 g/cm$^3$.

6. A capsule, cartridge or container in accordance with claim 1 wherein more than 90% of said drug particles are less than 60 microns in diameter and said drug has a loose bulk density greater than 0.3 g/cm$^3$.

7. A capsule, cartridge or container in accordance with claim 1 wherein more than 90% of said drug particles are less than 60 microns in diameter and said drug has a packed density of 0.4 to 0.75 g/cm$^3$.

8. A capsule, cartridge or container in accordance with claim 1 wherein at least 50% of said drug particles are less than 10 microns in diameter.

9. A capsule containing a finely divided inhalation formulation comprising a therapeutically effective proportion of individual particles consisting essentially of sodium cromoglycate, in unagglomerated form and capable of penetrating deep into the lung, at least 50% by weight of said particles having diameters less than 60 microns, said particles being sufficiently free-flowing to be filled into said capsule on an automatic filling machine and to empty from an opened capsule in an inhalation device, a substantial proportion of the individual drug particles having a ring doughnut shape, the permeametry:BET ratio of the particles being in the range of 0.5 to 1.0.

10. A method of administering sodium cromoglycate to a patient by way of inhalation comprising rotating and vibrating an opened capsule according to claim 1, in an air stream which is inhaled by the patent.

* * * * *